(12) United States Patent
Virtanen

(10) Patent No.: US 9,873,800 B2
(45) Date of Patent: Jan. 23, 2018

(54) TUNABLE MATERIALS

(71) Applicant: TESLA NANOCOATINGS, INC., Massillon, OH (US)

(72) Inventor: Jorma A. Virtanen, Massillon, OH (US)

(73) Assignee: Tesla Nanocoatings, Inc., Massillon, OH (US)

( * ) Notice: Subject to any disclaimer, the term of this patent is extended or adjusted under 35 U.S.C. 154(b) by 0 days.

(21) Appl. No.: 15/605,453

(22) Filed: May 25, 2017

(65) Prior Publication Data

US 2017/0260401 A1    Sep. 14, 2017

Related U.S. Application Data

(62) Division of application No. 14/410,009, filed on Dec. 19, 2014, now Pat. No. 9,725,603.

(51) Int. Cl.
| | |
|---|---|
| *C09D 5/08* | (2006.01) |
| *C09C 1/48* | (2006.01) |
| *C09C 1/46* | (2006.01) |
| *B82Y 40/00* | (2011.01) |
| *B82Y 30/00* | (2011.01) |
| *C07D 303/30* | (2006.01) |
| *C07F 7/18* | (2006.01) |
| *C09D 5/10* | (2006.01) |
| *C01B 31/02* | (2006.01) |
| *C01B 31/04* | (2006.01) |
| *C09C 1/56* | (2006.01) |

(52) U.S. Cl.
CPC ............... *C09D 5/08* (2013.01); *B82Y 30/00* (2013.01); *B82Y 40/00* (2013.01); *C01B 31/0273* (2013.01); *C01B 31/0484* (2013.01); *C07D 303/30* (2013.01); *C07F 7/1836* (2013.01); *C09C 1/46* (2013.01); *C09C 1/48* (2013.01); *C09C 1/565* (2013.01); *C09D 5/084* (2013.01); *C09D 5/106* (2013.01); *C01P 2004/13* (2013.01)

(58) Field of Classification Search
None
See application file for complete search history.

(56) References Cited

U.S. PATENT DOCUMENTS

| | | | |
|---|---|---|---|
| 9,243,146 B2 | 1/2016 | Virtanen | |
| 2004/0071624 A1* | 4/2004 | Tour | B82Y 30/00 423/447.1 |
| 2004/0265755 A1 | 12/2004 | Park et al. | |
| 2005/0019791 A1 | 1/2005 | Jung et al. | |
| 2007/0111015 A1 | 5/2007 | Avakian et al. | |
| 2007/0298669 A1 | 12/2007 | Barrera et al. | |
| 2009/0042136 A1* | 2/2009 | Tour | B82Y 10/00 430/296 |
| 2009/0171106 A1* | 7/2009 | Virtanen | B82Y 40/00 549/512 |
| 2009/0318717 A1 | 12/2009 | Virtanen et al. | |
| 2010/0209330 A1 | 8/2010 | Golzhauser et al. | |
| 2010/0276630 A1* | 11/2010 | Chandrasekhar | B22F 1/025 252/74 |
| 2011/0027497 A1* | 2/2011 | Rueckes | B82Y 30/00 427/535 |

FOREIGN PATENT DOCUMENTS

| | | |
|---|---|---|
| FI | 2012 0198 | 6/2012 |
| WO | 2007 143 028 | 12/2007 |
| WO | 2009 048 596 | 4/2009 |
| WO | 2013 191 809 | 12/2013 |

OTHER PUBLICATIONS

Spitalsky, Z., Tasis, D., Papagelis, K., Galiotis, C., "Carbon Nanotube-Polymer Composites: Chemistry, Processing, Mechanical and Electrical Properties" Progress in Polymer Science 35, 2010, pp. 357-401.
Ge, J.J., Zhang, D., Li, Q., Hou, H., Graham, M.J., Dai, L., Harris, F.W., Cheng, S.Z.D., "Multiwalled Carbon Nanotubes with Chemically Grafted Polyetherimides" American Chemical Society, 2005, 127, pp. 9984-9985.
Roy, N., Sengupta, R., Bhowmick, A.K., "Modifications of Carbon for Polymer Composites and Nanocomposites" Progress in Polymer Science 37, 2012, pp. 781-819.
Syrgiannis, Z., Gebhardt, B., Ootzer, C., Hauke, F., Graupner, R., Hirsch, A., "Reductive Retrofunctionalization of Single-Walled Carbon Nanotubes" Angew. Chem. Int. Ed. 2010 49, pp. 3322-3325.
Wu, et al., "Targeted Delivery of Amphotericin B to Cells by Using Functionalized Carbon Nanotubes," Agnew. Chem. Int., Ed. 2005, 44, 6358-6362.
Nayak, et al., "A Novel Route for Polystyrene Grafted Single-Walled Carbon Nanotubes and their Characterization," Macromolecular Chemistry and Physics, 2008, 209, 1137-1144.

* cited by examiner

*Primary Examiner* — Sheeba Ahmed
(74) *Attorney, Agent, or Firm* — Emerson Thomson Bennett LLC; Daniel A. Thomson

(57) ABSTRACT

One or more techniques are disclosed for a method for functionalized a graphitic material comprising the steps of: 1) providing a graphitic material; 2) providing a first molecule comprising a first group, a spacer, and a second group; 3) providing a second molecule comprising a third group, a spacer, and a fourth group, wherein said third group is a different group from said first group; and 4) bonding the first molecule and the second molecule to the graphitic material. Also disclosed is a tunable material composition comprising the functionalized carbon nanotubes or functionalized graphene prepared by the methods described herein.

14 Claims, 10 Drawing Sheets

TUNABLE MATERIALS

This application is a divisional application of U.S. Ser. No. 14/410,009, filed Dec. 19, 2014, which is a 371 national stage entry of PCT/US2013/038852, filed Apr. 30, 2013, which claims priority to U.S. Ser. No. 61/850,861, entitled TUNABLE MATERIALS, filed Feb. 20, 2013, and Finland Serial No. 201201980993, entitled TUNABLE MATERIALS, filed Jun. 21, 2012.

BACKGROUND

Composites may be fabricated with thermoset plastics such as epoxies, polyurethanes, and silicones. Epoxies may be produced by reacting an epoxy resin and a hardener. Polyurethane polymers can be formed by reacting an isocyanate with a polyol. Silicones may comprise polymerized siloxanes with organic side groups.

Carbon nanotubes (CNTs) and graphene have been used to reinforce thermoset plastics like epoxies, polyurethanes, silicones, and other resins and polymers. CNTs, functionalized CNTs (or hybrid CNTs, denoted HNTs), graphene, and functionalized graphene may collectively be referred to as hybrid graphitic materials (HGMs). These HGMs can be incorporated into any of the epoxy components such as the epoxy resin and hardener. HGMs may also be incorporated into polyurethanes and silicones.

Thermoset plastics, CNTs, graphene, and HNTs may increase modules and toughness, but elasticity may be preferred for certain plastic composites. In order to increase elasticity, siloxane may be added. Siloxane backbone may be coiled, and it can be covered by alkyl or aryl groups in silicones. Thus, silicones can be very flexible and hydrophobic. Hydrophobicity can be increased by functionalization with groups such as fluorinated alkyl or aryl groups.

Numerous functionalization methods for the CNTs have been developed. These include nitric acid/sulfuric acid oxidation of the CNTs, aryl radical addition to the CNTs, ball milling induces addition of amines and sulfides into the CNTs, butyl lithium activated coupling to alkyl halides, and ultrasonic vibration assisted addition of many reagents, including amines, and epoxies. Improving mechanochemical reactions, such as mechanical or ultrasound cutting, may induce chemical reactions of the CNTs.

An anticorrosive coating may contain sacrificial metal particles, such as zinc particles. The concentration of the particles may exceed the percolation limit, which is about 30% for spherical particles. High concentration of these particles can reduce the integrity of the coating, especially if the particles are not chemically bound with the polymer. Anticorrosive coatings may use sacrificial metal particles that are electrically connected with a coated metal surface through a CNT or graphene network. Using the CNT or graphene network may require less sacrificial metal particles within an anticorrosive coating. Additionally, the graphitic material may be coated with a metal layer. The metal layer may be comprised of nanoparticles or microparticles. The metal particles may be coated with a thin oxide layer unless the graphitic material is coated in the absence of oxygen. With the nanoparticles, the oxide layer can be a relatively large part of the particle. The oxide layer may also be a large portion for a metal coating around a CNT. Besides metallic particles, the particles may also be ceramic.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

In one implementation, a method of modifying a graphitic material comprising the steps of: 1) providing a graphitic material; 2) providing a first molecule comprising a first group, a spacer, and a second group; 3) providing a second molecule comprising a third group, a spacer, and a fourth group, wherein said third group is a different group from said first group; and 4) bonding the first molecule and the second molecule to the graphitic material.

To the accomplishment of the foregoing and related ends, the following description and annexed drawings set forth certain illustrative aspects and implementations. These are indicative of but a few of the various ways in which one or more aspects may be employed. Other aspects, advantages and novel features of the disclosure will become apparent from the following detailed description when considered in conjunction with the annexed drawings.

BRIEF DESCRIPTION OF THE DRAWINGS

What is disclosed herein may take physical form in certain parts and arrangement of parts, and will be described in detail in this specification and illustrated in the accompanying drawings which form a part hereof and wherein.

DETAILED DESCRIPTION

Figure 1:
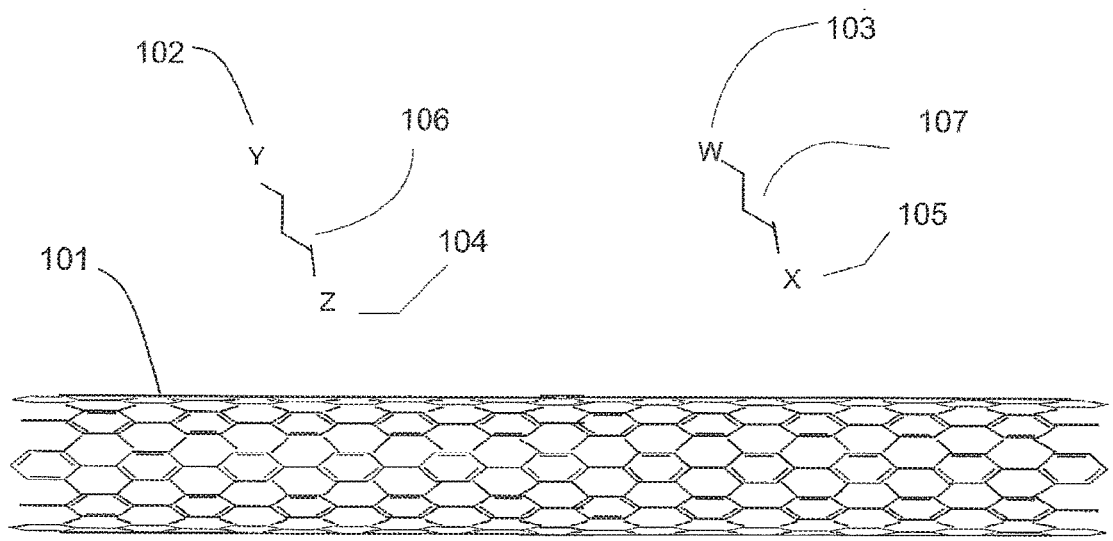
FIG. 1 is a plain view of the process disclosed herein.
Figure 1:
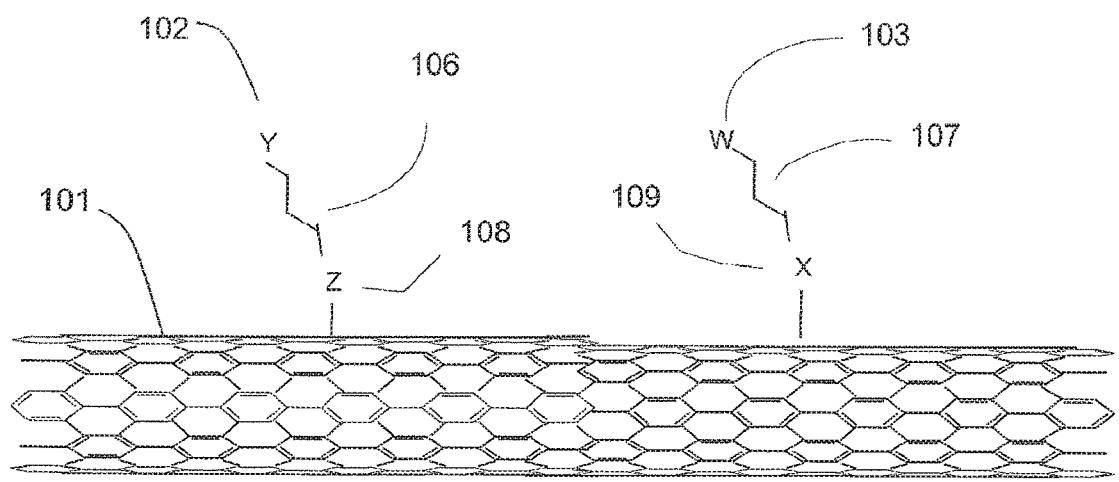

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

The word "exemplary" is used herein to mean serving as an example, instance or illustration. Any aspect or design described herein as "exemplary" is not necessarily to be construed as advantageous over other aspects or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Further, at least one of A and B and/or the like generally means A or B or both A and B. In addition, the articles "a" and "an" as used in this application and the appended claims may generally be construed to mean "one or more" unless specified otherwise or clear from context to be directed to a singular form.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. Of course, those skilled in the art will recognize many modifications may be made to this configuration without departing from the scope or spirit of the claimed subject matter.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure.

In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

Both carbon nanotubes (also referred to as CNTs) and graphene are graphitic materials.

They are substances composed essentially of pure carbon. The edges of the CNTs and graphene may have other elements, such as hydrogen and oxygen. Graphene may have atoms arranged in a regular hexagonal pattern similar to graphite, but in one-atom fixed sheet. Graphene may be comprised of carbon atoms, where each carbon atom is bonded with three other carbon atoms. The carbon atom may form four covalent bonds, where each carbon has both a single and double bond. These covalent bonds can provide strength within the graphene material. It can be very light in weight, but can provide strength as a material. Even with small quantities of graphitic materials added to a composite, the tensile strength of the composite may be increased. In addition to their strength, graphitic materials are also known for their electronic conductance.

Generally, graphitic materials may be smooth and regularly shaped, but may slip easily within the nanocomposite. Slipping may be prevented by functionalizing graphitic materials. Proper functionalization can allow covalent, coordination, or ionic bond formation between functionalized graphitic material, various particles, polymers, and the surface to be protected by the coating.

Graphene can be fabricated in two different ways, either from smaller building blocks (bottom-up), or exfoliating graphite (top-down). Bottom-up method allows fabrication of continuous graphene layers on a substrate. That is ideal method for the fabrication of transistors and electronic circuits. For large scale materials fabrication, exfoliation of graphite can be a more suitable approach. Exfoliating can be done by separating graphene layers by intercalating hydrogen or some other atoms or ions into graphite, or by ultrasonic vibration. The edge of graphene sheet contains other atoms than carbon, for example, hydrogen or oxygen. The edge can be functionalized deliberately by any functional group.

Carbon nanotubes are also a graphitic material but with a cylindrical structure. Each CNT is a molecule with a certain structure which may or may not be exactly known. CNTs can be durable, and they can resist nanocracking due to thermal expansion and other contraction cycles when used in composites or coatings. Carbon nanotubes may have a high tensile strength compared to many other materials. They may also increase the tensile strength of composites, even when they are added to the composites in small quantities. In addition, CNTs may have an increased persistence length. Persistence length is a mechanical property measurement quantifying the stiffness of a polymer.

Most polymers can have a persistence length of about 1 nm to about 2 nm. However, multiwalled carbon nanotubes (MWNTs) can have persistence length more than about 100 nm. Single-walled carbon nanotubes (SWNTs) and double-walled carbon nanotubes (DWNTs) may have an increased persistence length as well. Both the high tensile strength and persistence length can allow graphitic materials to provide tensile strength for nanocomposites, especially if they may be chemically bonded with a polymer or particles that can be part of the composition described herein.

Functionalized CNTs may be fundamentally different than the CNTs that may be used as a starting material. Functionalized CNTs may also be different than CNTs that have not been functionalized. Functionalized CNTs may be molecules that can have different chemical structures, chemical, and physical properties than CNTs. For comparison, cellulose and functionalized celluloses, such as carboxymethyl cellulose (CMC), may have different properties. CMC may be chemically derived from cellulose, but it may not function like cellulose. CMC has totally different chemical and physical properties.

FIG. 1 provides a process of modifying graphitic material, comprising the steps of: 1) providing a graphitic material; 2) providing a first molecule comprising a first group, a spacer, and a second group; 3) providing a second molecule comprising a third group, a spacer, and a fourth group, wherein said third group is a different group from said first group; and 4) bonding the first molecule and the second molecule to the graphitic material. Within the process, the first group may comprise at least one group of hydroxyl, thiol, amino, epoxy, carboxyl, and silyl, and the second group may comprise at least one group of amino, epoxy, hydroxyl, carboxyl, silyl, and thiol. Also within the process described herein, the third group may comprise at least one group of thiol, carboxyl, trialkoxysilyl, phosphoryl ester, crown ether, cryptand, dioxime, and N-heterocycle, and the fourth group may comprise at least one group of amino, epoxy, hydroxyl, carboxyl, silyl, and thiol. The first group may be different than the third group within the graphitic material. The first molecule may be bound to the graphitic material before the second molecule, or the second molecule may be bound to the graphitic material before the first molecule. Additionally, the first molecule comprising a first group, a spacer, and a second group may bound simultaneously with the second molecule comprising a third group, a spacer, and a fourth group, as described in the method above. The first molecule may comprise at least one molecule of diamino compound, diepoxy compound, and amino alcohol compound. The second molecule may comprise at least one molecule of a diester of O-phosphorylethanolamine and aminopropyl trialkoxysilane.

Within the method shown in FIG. 1, the graphitic material can be functionalized. The graphitic material may be at least one graphitic material of graphene and CNTs. For FIG. 1, a CNT 101 may be depicted as the graphitic material.

The first group 102 (denoted as Y) may be comprised of at least one group of hydroxyl, thiol, amino, epoxy, carboxyl, and silyl. Examples of the first group 102 for silyl may include, but are not limited to, dimethylsilyl, and diphenylsilyl.

The third group 103 (denoted as W) may be comprised of at least one group of thiol, carboxyl, trialkoxysilyl, phosphoryl ester, crown ether, cyclopetadienyl, cryptand, dioxime, and N-heterocycle. Examples of the third group 103 may include, but are not limited to, phosphoryl di(trichloroethyl) ester, phosphoryl di(cyanoethyl) esters, 18-crown-6, 2,2,2-cryptand, 2,1,1-cryptand, dimethylglyoxime, and phenantrolinyl. For specific metals, cyclopentadienyl may bind to iron, imidazolyl may bind to iron, 18-crown-6 may bind to magnesium, 2,2,2-cryptand may bind to zinc, imidazolyl may bind to zinc, 2,1,1-cryptand may bind to magnesium, dimethylglyoxime may bind to nickel, imidazolyl may bind to copper, and phenantrolinyl may bind to copper. Several other ligands well known in the art may also be used.

The second group 104 (denoted as Z) and fourth group 105 (denoted as X) comprises at least one group of amino, epoxy, hydroxyl, carboxyl, silyl, and thiol. Examples of the second group 104 and fourth group 105 for silyl may include, but are not limited to, dimethylsilyl and diphethylsilyl.

Within the first molecule, a spacer 106 may be bound between the first group 102 (denoted as Y) and the second group 104 (denoted as Z). The spacer 106 of the first molecule may vary. The spacer may be different for the first molecule and second molecule. For example, the spacer may be a propylene spacer, as shown in FIG. 1. The spacer 106 may be less than about 1 nm. The length of the spacer 106 may still allow for electron tunneling when the spacer 106 is less than about 1 nm. Also, the first group Y 102, third group W 103, or both the first group Y 102 and third group W 103 may be bound to the spacer 106 such that the first group Y 102, third group W 103, or both the first group Y 102 and third group W 103 may be in contact with the CNT 101.

36. The spacer 107 of the second molecule may also vary. Within the second molecule, a spacer 107 may be bound between the third group 103 (denoted as W) and the fourth group 105 (denoted as X). For example, the spacer may be a propylene spacer, as shown in FIG. 1. The spacer 107 may be less than about 1 nm. The length of the spacer 107 may also still allow for electron tunneling when the spacer 107 is less than about 1 nm. Also, the first group Y 102, third group W 103, or both the first group Y 102 and third group W 103 may be bound to the spacer 107 such that the first group Y 102, third group W 103, or both the first group Y 102 and third group W 103 may be in contact with the CNT 101.

Further, polymerizing may occur onto the first group Y 102. Polymerization may also occur onto the third group W 103 unless third group W 103 may be a specific metal binding ligand. Polymerization may include a polyurethane, an epoxy, or a silicone. A sacrificial metal particle may be bound to the third group W 103. The sacrificial metal particle may comprise at least one metal of zinc, magnesium, nickel, aluminum, and cobalt. Within the methods described herein, the sacrificial metal particle may be in electrical contact with the graphitic material. Within the electrical contact, the spacer may be less than about 1 nm in length, and electron tunneling may occur.

The method described herein in FIG. 1 may allow at least two different types of molecules to be bound to a graphitic material. Bonding may be provided by at least one method of mechanical milling, ultrasonic vibration, and high pressure microfluidic injection. Instead of providing a mixture of graphitic materials where only one type of molecule may be bound to a graphitic material, the method described herein may permit a single functionalized graphitic material to be used. The amount and ratio of binding for both the first and second molecules may be tailored for a specific application.

The functionalized graphitic material may also be incorporated into a plastic composite. The plastic composite may be thermoset. The plastic composite comprises at least one resin of epoxy, polyacrylate, polyurethane, and phenolformaldehyde. The plastic composite may be a tunable material composition. The tunable material may comprise: 1) a thermoset plastic; and 2) a graphitic material prepared by the method comprising the steps of: a) providing a graphitic material; b) providing a first molecule comprising a first group, a spacer, and a second group; c) providing a second molecule comprising a third group, a spacer, and a fourth group, wherein said third group is a different group from said first group; and d) bonding the first molecule and the second molecule to the graphitic material. Within the process for providing a first molecule, the first group may comprise at least one group of hydroxyl, thiol, amino, epoxy, carboxyl, and silyl, and the second group may comprise at least one group of amino, epoxy, hydroxyl, carboxyl, silyl, and thiol. Also within the process described herein for providing a second molecule, the third group may comprise at least one group of thiol, carboxyl, trialkoxysilyl, phosphoryl ester, crown ether, cryptand, dioxime, and N-heterocycle, and the fourth group may comprise at least one group of amino, epoxy, hydroxyl, carboxyl, silyl, and thiol. The first group may be different than the third group within the graphitic material. The tunable material composition can be used in anticorrosive coatings in electromagnetic interference shields, magnetic shields, conductors, super capacitors, pre-impregnated composites, epoxies, polyacrylates, and polyurethanes. The composition may also comprise a silicone.

Within the composition described above, the thermoset plastic may be at least one plastic of an epoxy, polyacrylates, polyurethane, and phenolformaldehyde. The graphitic material may be at least one carbon of carbon nanotubes and graphene.

Further, the graphitic material can be functionalized. The graphitic material can be functionalized with at least one hardener of diaminobenzene, diamino polyethyleneoxide, diamino polypropyleneoxide, diamine cyclohexane derivatives, and aminated tall oil. The graphitic material may be functionalized in the absence of oxygen and water.

The composition described above may further comprise at least one particle of macroparticles, microparticles, and nanoparticles. The macroparticles can comprise at least one macroparticle of sand, glass, basalt, alumina, silica, titanium dioxide, ceramic, and graphite fibers. The microparticles comprise at least one microparticle of titanium dioxide, silica, ceramic, graphite, iron phosphate, alumina, nickel, cobalt, zinc, aluminum, and magnesium. The nanoparticles comprise at least one nanoparticle of titanium dioxide, copper oxide, iron phosphate, silver, silica, and alumina.

Figure 2:
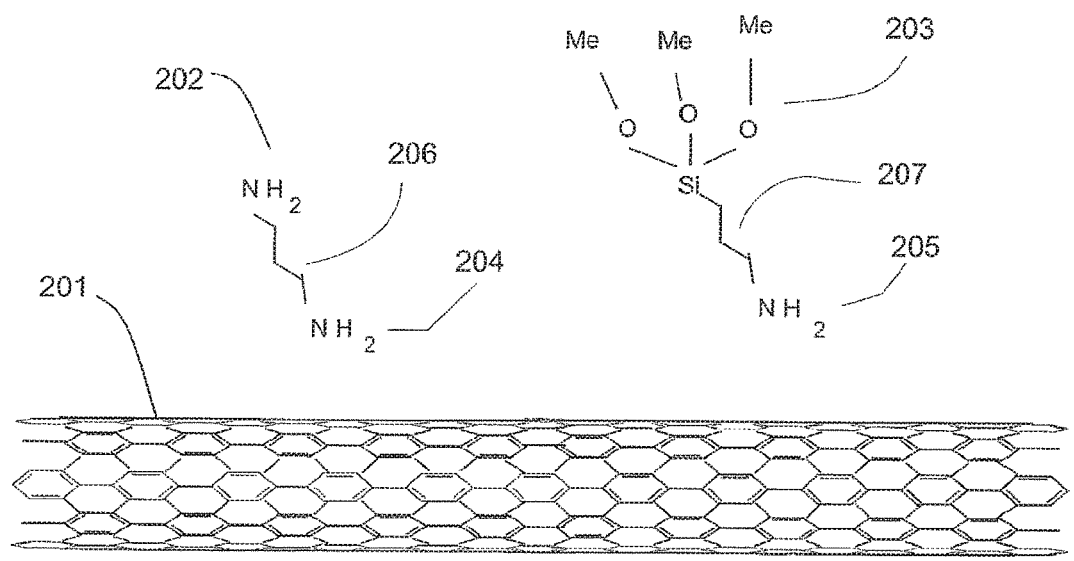
FIG. 2 schematically illustrates what is disclosed herein.
Figure 2:
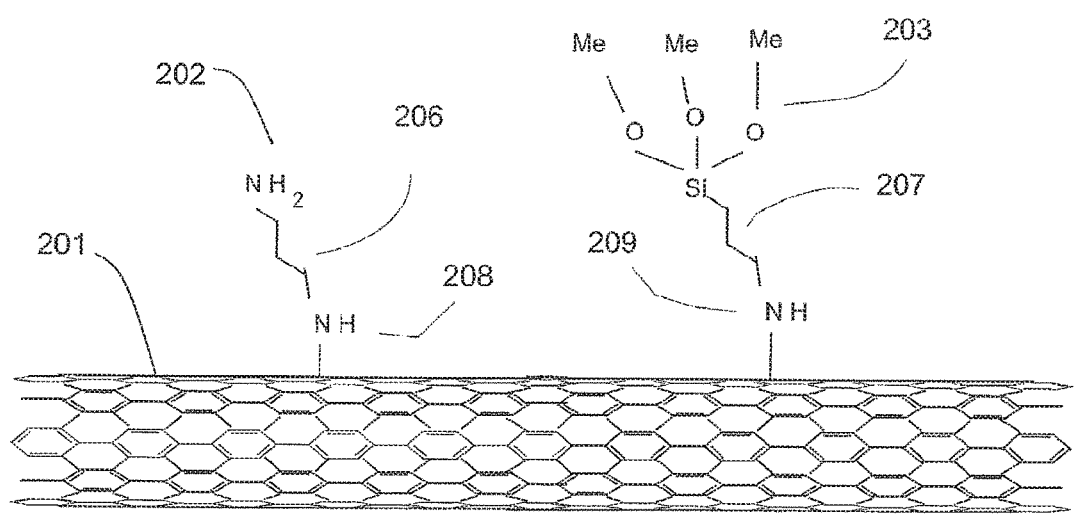

FIG. 2 also provides an embodiment of the method described herein for a process of modifying graphitic carbon, comprising the steps of: 1) providing a graphitic material; 2) providing a first molecule comprising a first amino group, a spacer, and a trialkoxysiloxane group; 3) providing a second molecule comprising a second amino group, a spacer, and a third amino group; and 4) bonding the first amino group and the second amino group to the graphitic material. Alternatively, the method of FIG. 2 described herein may be a process of modifying graphitic carbon, comprising the steps of: 1) providing a graphitic material; 2) providing a first molecule comprising a second amino group, a spacer, and a third amino group; 3) providing a second molecule comprising a first amino group, a spacer, and a trialkoxysiloxane group; and 4) bonding the first amino group and the second amino to the graphitic material. Additionally, the molecule may comprise a first amino group, a spacer, and a trialkoxysiloxane group may be added simultaneously with the molecule comprising a second amino group, a spacer, and a third amino group, both described in the two methods above. The first molecule may be bound to the graphitic material before the second molecule, or the second molecule may be bound to the graphitic material before the first molecule. Additionally, the first molecule comprising a first group, a spacer, and a second group may be bound simultaneously with the second molecule comprising a third group, a spacer, and a fourth group, as described in the method above. Bonding may be provided by at least one method of mechanical milling, ultrasonic vibration, and high pressure microfluidic injection.

Within the method shown in FIG. 2, the graphitic material can be functionalized. The graphitic material may be at least one graphitic material of graphene and CNTs. For FIG. 2, a CNT 201 may be depicted as the graphitic material.

The top illustration in FIG. 2 provides the introduction of both the amino group 202 and the trialkoxysiloxane group 203 to the CNT 201. Within the method, both the amino group 202 and the trialkoxysiloxane group 203 may then be bonded to the CNT 201 with a spacer (206 and 207), as shown in the bottom illustration in FIG. 2. Specifically, the diamino compound may bind through the amine group 204 to the CNT 201 to form a secondary amino group 208. Similarly, the second molecule may also bind through the amine group 205 to the CNT 201 to form a secondary amino group 209.

The spacer portion of the molecule may vary. For example, the spacer may be a propylene spacer, as shown in FIG. 2. The spacer may be different for the first molecule and second molecule. The binding of both the amino group 202 and trialkoxysiloxane group 203 may occur due to the functionalization of an amino group with both the amino group 202 and trialkoxysiloxane group 203. The amino group may be bound directly to the CNT 201, allowing both the amino group 202 and trialkoxysiloxane group 203 to then functionalize the CNT 201.

The amino group 202 may then provide a starting point for further epoxy and urethane functionalities, and the both trialkoxysiloxane group 203 may provide a starting point of silicone functionalities. The epoxy and urethane functionalities as well as other amino functionalities may provide a rigidity and toughness to the CNT 201, while the silicone functionalities may provide a softness and flexibility to the CNT 201. Together, the multiple functionalities within the CNT 201 may provide desired properties and also a means to tailor the properties to a specific application. For example, an amino group may be polymerized with an epoxy monomer, epoxy oligomer, urethane monomer, or urethane oligomer. Also, the trialkoxysiloxane group may be polymerized with silicone monomer or oligomer.

The graphitic material may be functionalized with at least one hardener of diaminobenzene, diamino polypropyleneoxide, diamine cyclohexane derivatives, and aminated tall oil. The graphitic material may also be functionalized with another curing agent. The graphitic material may also be functionalized in the absence of oxygen and water.

Figure 3:
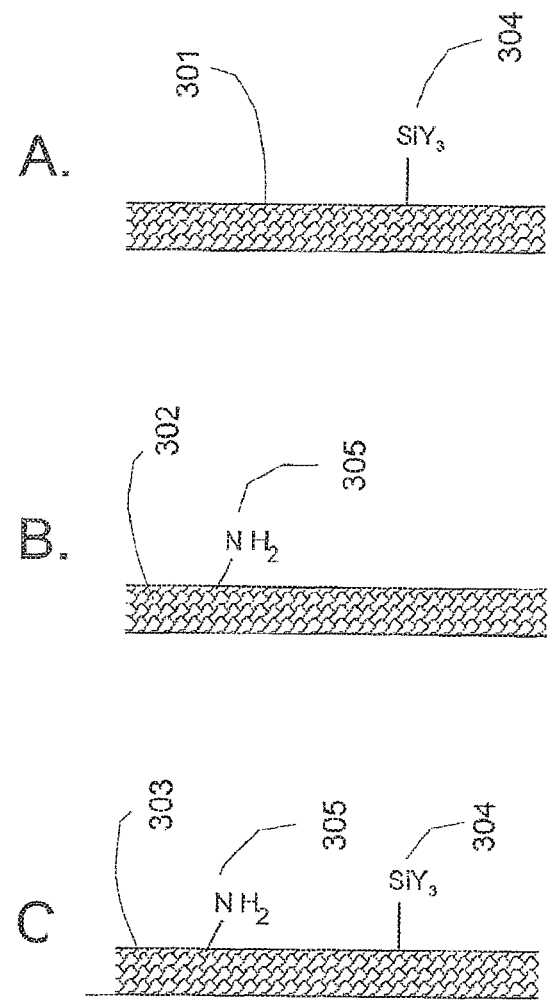
FIG. 3 schematically illustrates what is disclosed herein.

FIG. 3 shows various versions of functionalizing CNTs with polymers. A polymer may be connected through a primary or secondary amino group, hydroxyl group, or epoxy group. The hydroxyl group may include a phenolic hydroxyl group. These functionalities may serve as starting points for polyurethane, polyacrylate, polyurea, epoxy resin, phenol-formaldehyde resin, polyacrylates, or other polymers. One embodiment of the general principle of the method described herein is a CNT, or graphene sheet that is functionalized with alkoxysilane, or amino functionalities, or simultaneously with both of these.

Each functionalized CNT or graphene sheet may contain tens or hundreds functional groups being able to bind each particle multiple times. Each functionalized CNT or graphene sheet may also bind multiple particles. Similarly, each functionalized CNT or graphene sheet may bind multiple polymer chains. These functionalities may be directly connected with CNTs or graphene, or spacers may be used. Spacer may contain aliphatic, aromatic or heterocyclic moieties.

In FIG. 3A, the CNT 301 may be functionalized with only the trialkoxysiloxane group 304. If only the trialkoxysiloxane group 304 may be used, then only silicone functionalities may be bound. In FIG. 3B, the CNT 302 may be functionalized with only the amino group 305. If only the amino group 305 may be used, then only epoxy, urethane, and other amino functionalities may be bound. Although a mixture of the functionalized CNT 301 and CNT 302 may be used in an application, neither provides both the amino group 305 and trialkoxysiloxane group 304 within a single CNT or other graphitic material. FIG. 3C shows the method described herein, where the CNT 303 may be functionalized with both the amino group 305 and the trialkoxysiloxane group 304.

Figure 4:
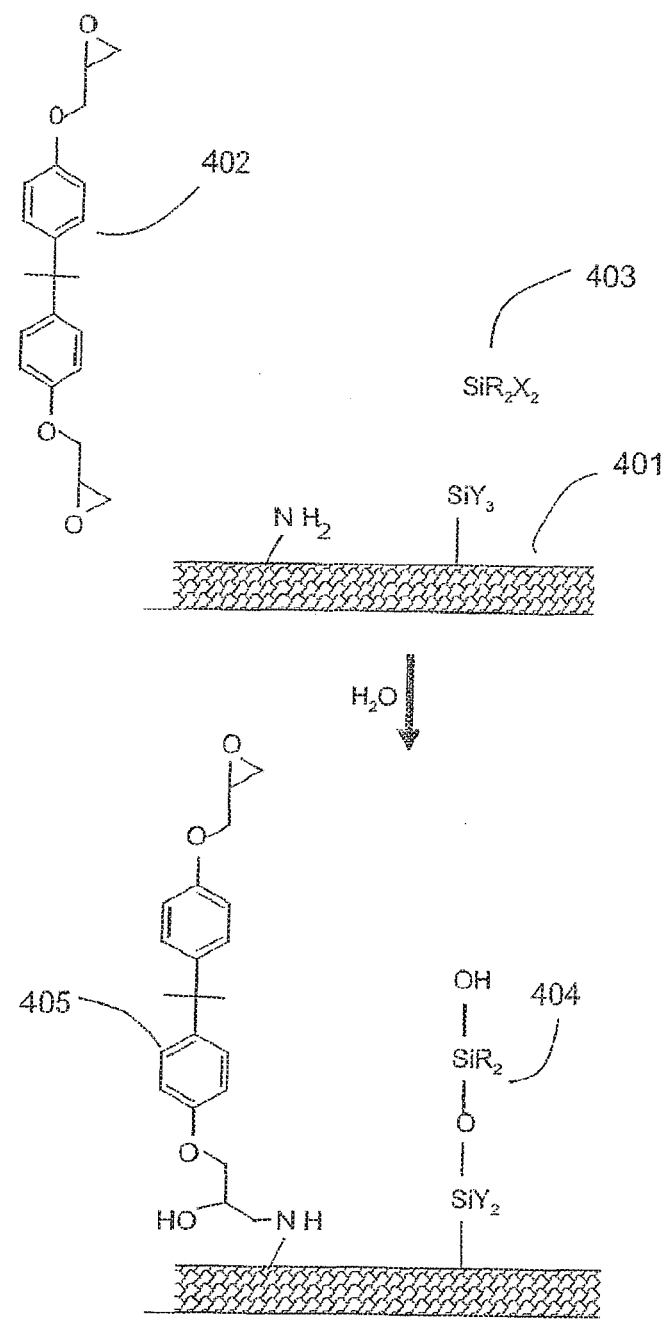
FIG. 4 schematically illustrates what is disclosed herein
FIG. 5 schematically illustrates what is disclosed herein.

FIG. 4 may illustrate how side chains may be grown onto the graphitic material. In the beginning of the reaction shown at the top of FIG. 4, the CNT 401 may contain both the amino group and trialkoxysiloxane group bound to it. In this example, the silicone 403 may be reacted in the presence of a catalytic amount of water. The reaction illustrated in FIG. 4 may allow for later polymerization of epoxy 402 and silicone 403, but polyurethane may also be polymerized in place of epoxy 402. From this reaction, both the epoxy functionality 405 and the silicone functionality 404 may then provide different properties to the CNT 401.

Figure 5:
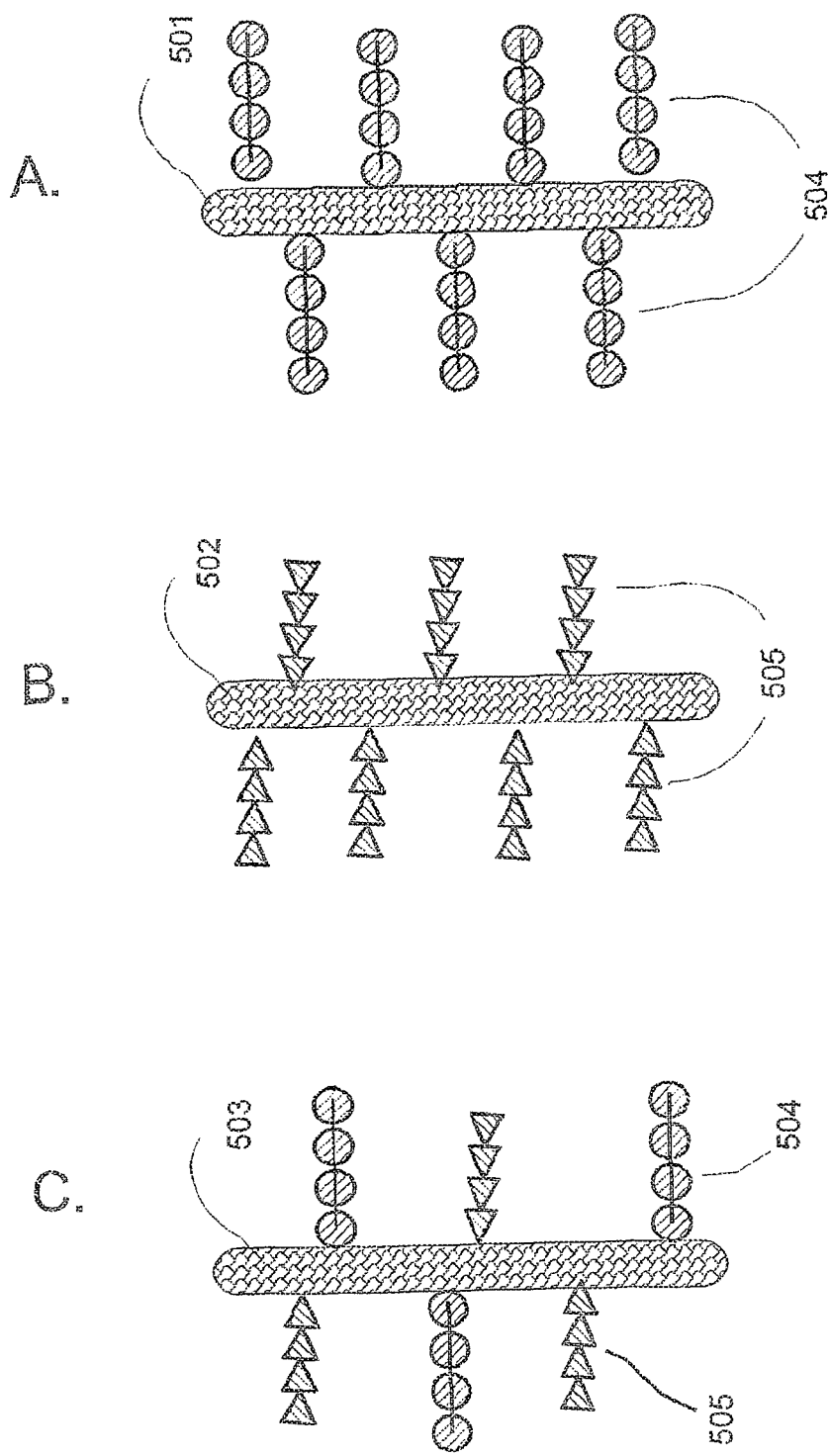

FIG. 5 may provide three different pictorial representations of how the chains may be grown onto the graphitic material. In this figure, the graphitic material can be the CNT 501. In FIG. 5A, the CNT 501 may have multiple silicone group side chains 504. In FIG. 5B, the CNT 502 may have multiple epoxy or polyurethane side chains 505. FIG. 5C provides the CNT 503 which may comprise both epoxy or polyurethane side chains 505 and silicone group side chains 504. In general, these various side chains can be grafted onto the CNT. The side chains may be branched. If the polymer chains are sufficiently different physically, chemically, or both physically and chemically, such as in FIG. 5C, the CNT 503 may separate and form layered structure, as further described in FIG. 6. These layers may be weakly bound, or strongly bound, if a biphasic CNT is included into a composition. This kind of biphasic CNT may contain at least two types of branches that are able to interact strongly with both layers, potentially allowing the fabrication of self-stratifying coatings.

Described herein in FIG. 5C can allow for the combination of both hard and soft plastic composites and coating materials with functionalized CNTs. The plastic composites may be thermoset. The plastic composites may include epoxies, polyurethanes, polyacrylates, and phenolformaldehyde. These coatings can be impact and crack resistant. Although abrasion resistance may be acceptable, it may be improved by covalently linking nanoparticles or microparticles.

Figure 6:
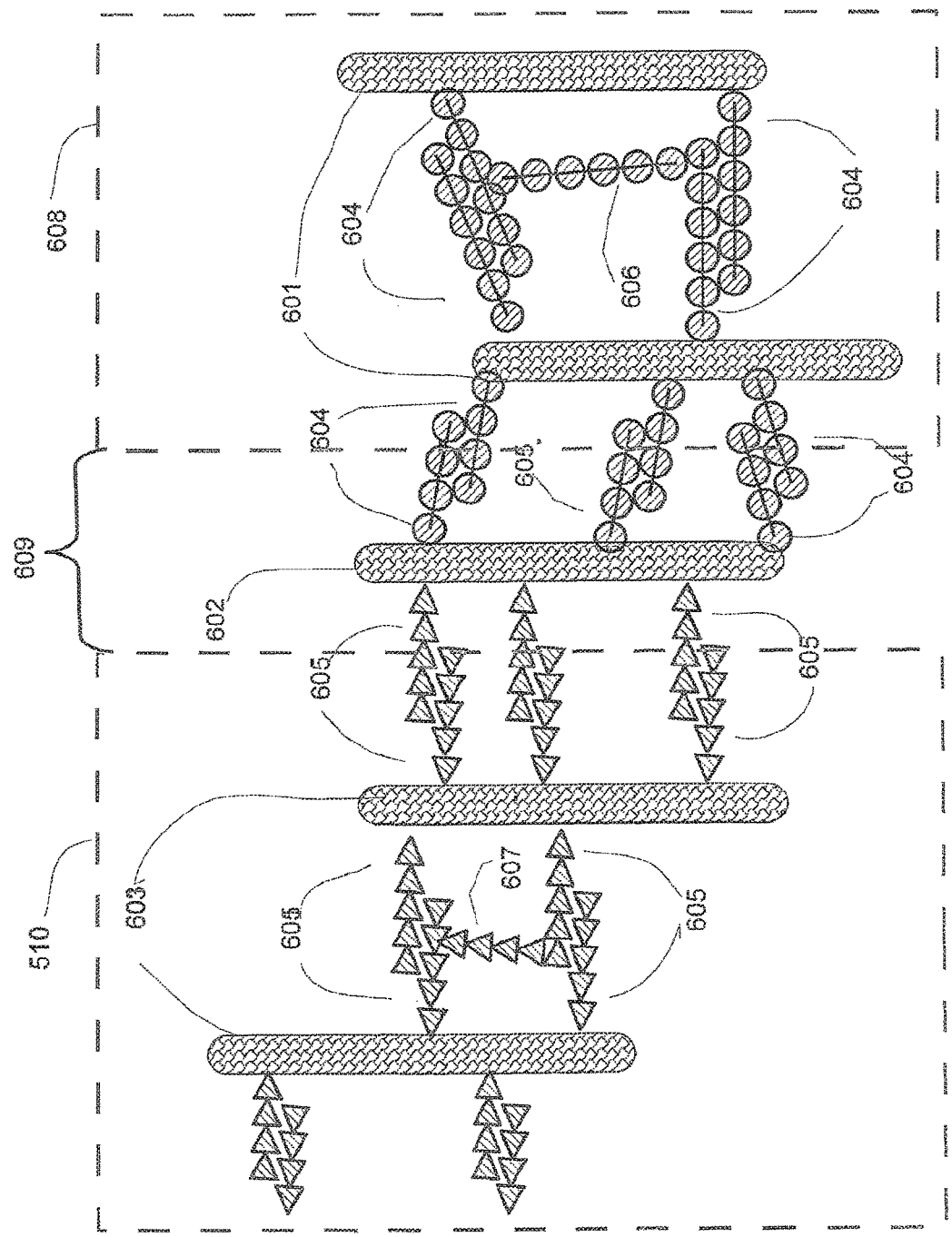
FIG. 6 schematically illustrates what is disclosed herein.

In FIG. 6, multiple layers of CNTs may be demonstrated. The CNTs (601, 602, and 603) are provided within the figure. The separate layers of functionalized CNTs, labeled as 608 and 610 within the figure, may be as a result of the stratification of the functionalized CNTs. An intermediate area 609 may be located within the separate CNT layers of 608 and 610. The intermediate layer 609 may be used to bind the separate functionalized CNT layers 608 and 610 together. The layers may form when silicone layer 608 separates from the epoxy layer 610. Namely, the methyl groups within the silicone may provide layers. However, the phenyl groups within the silicone may prevent layers from forming especially if phenyl groups have polar substituents, such as methoxy. There may be only methyl groups within the silicone or only phenyl groups within the silicone. There may also be both methyl and phenyl groups within the silicone. If the layers may be formed, they may be as thin as about 10 nm. The layers may also be about 50 nm to about 50 μm.

The degree of the functionalization of carbon nanotubes can be adjusted in a wide range of moieties covalently bound per micrometer of a carbon nanotube. For example, the functionalities may be amino groups that can initiate the polymerization of an epoxy compound. The functionalities may also be amino groups that can initiate the polymerization of a polyurethane compound. The functionalities may be trialkoxysiloxane groups that can initiate the polymerization of a silicone.

Within the layers, there may be interaction between the amino group side chains 605, 607 and trialkoxysiloxane group side chains 604 and 606. Because of these interactions, there may be binding and crosslinking between the functionalized CNTs.

The layered structure provided in FIG. 6 may allow for coatings that resist cracking since they can be less rigid because of the silicone groups. The layered structure may also assist in applications in which a layered structure may be advantageous. For instance, these layered structures may be used in ship coatings in which barnacles may peel off at least one layer of the coating at a time, but the layered structure can remain within coating. Aromatic or aliphatic curing agents may also be used within the layered structure.

The functionalized graphitic material may be bound with a polymer, a metal particle, or both. The method described herein may allow more electrical conduction than a mere mixing of components. If electrical contact between a particle and graphitic material is desired, the spacer may be short.

Figure 7:
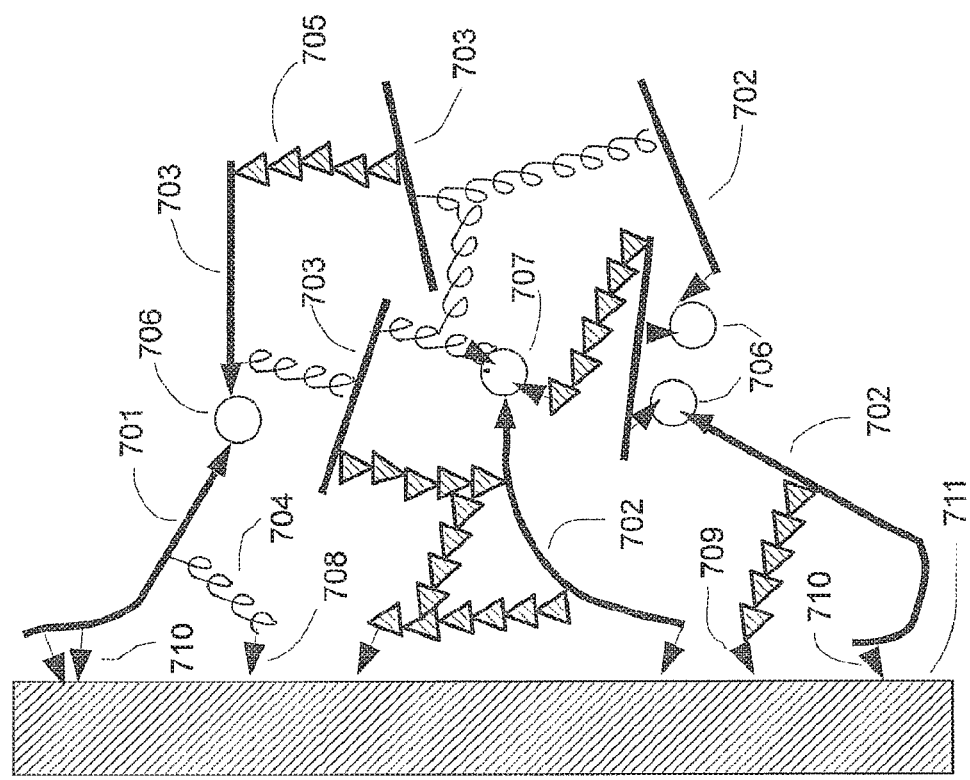
FIG. 7 schematically illustrates what is disclosed herein.

FIG. 7 may provide one embodiment of a structural representation of a tunable coating or plastic composite. Anticorrosive coatings may be an application of the process described herein. The tunable material composition in FIG. 7 may comprise: 1) a thermoset plastic; 2) silicone; and 3) at least one functionalized graphitic material of carbon nanotubes and graphene prepared by the method comprising the steps of: 1) providing a graphitic material; 2) providing a first molecule comprising a first amino group, a spacer, and a trialkoxysiloxane group; 3) providing a second molecule comprising a second amino group, a spacer, and a third amino group; and 4) bonding the first amino group and the second amino to the graphitic material. Alternatively, the method of providing at least one functionalized graphitic material may be prepared by other methods described above in FIG. 2. The first molecule may be bound to the graphitic material before the second molecule, or the second molecule may be bound to the graphitic material before the first molecule. Additionally, the first molecule comprising a first amino group, a spacer, and a trialkoxysiloxane group may bound simultaneously with the second molecule comprising a second amino group, a spacer, and a third amino group, as described in the method above.

FIG. 7 may depict the molecular connections for the methods described herein. The elastic polymer 704 may be depicted as a spring (previously depicted as circles in FIG. 5A). The elastic polymer 704 may include siloxane functionalities. The more rigid polymer 705 may be shown as triangles in FIG. 7. The more rigid polymer 705 may include epoxy, polyurethane, polyacrylates, and phenolformaldehyde. The three types of functionalized CNTs 701, 702, and 703 may correspond to 501, 502, and 503 in FIG. 5. Polymer chains, including the elastic polymer 704 and the more rigid polymer 705, can form a bridge between two functionalized CNTs, or bind functionalized CNT with a particle 706 and 707. Particles 706 and 707 may be bound with functionalized CNTs through a short spacer. Arrows depict the binding of polymers (704 and 705) or functionalized CNTs (701, 702, and 703) with the particles (706 and 707) or substrate 709. Polymer chains may be cross-linked. If polymerization reactions are orthogonal, no block polymers or graft polymers may be formed.

The present description can further provide a method to prepare coatings. This method may comprise the steps of: 1) functionalizing CNTs or graphene with amine hardener, aminopropyl trimethoxysilane, macroparticles, microparticles, or nanoparticles, 2) mixing the functionalized CNT with epoxy to form a mixture, 3) coating the mold with the mixture, 4) injecting the bulk epoxy mixture into the mold, and 4) curing the mixture.

Siloxane 704 segments within FIG. 7 can be formed from monomers, or they can be oligomers which may be partially prepolymerized. These components can be mixed with hardener or epoxy or both. Suitable monomers may include di(methoxyphenyl), dimethoxysilane, dianisyl dimethoxysilane, dimethyl dimethoxysilane, diphenyl diethoxysilane, aminopropyl trimethoxysilane (also known as APTMS), and tetraethoxysilicate (also known as TES). However, monomers may also include almost any aliphatic or aromatic moiety as well as some of their functionalized forms, such as chlorinated and fluorinated derivatives. These monomers may be polymerized if there may be a catalytic amount of water present. APTMS and TES may provide branching points in siloxane chain. APTMS can, in addition, serve as both a starting and end point for siloxane polymerization. Too many covalent epoxy contacts may reduce or eliminate the elasticity of siloxane, and the concentration of free APTMS where it may not be bound to functionalized CNT's or nanoparticles, may be less than about 10% of all silane components. Another kind of silicone polymer may be formed, for example, from vinyl dimethylsilane in the presence of catalytic amount of platinum. By varying side groups, many other analogous monomers can be used. In order to provide a starting point in a functionalized carbon nanotube, aminopropyl dimethylsilane may be used. The end point may be functionalized with aminopropyl vinyl methylsilane. Several analogous molecules could be used instead of these examples. Additionally, an amino group may serve as both a starting and end point for epoxy polymerization.

Within a composition comprising graphitic material and metal particle, the electrical contact between the metal particle and the graphitic material may be weak. This weakness may be due to layer of polymer wrapped around the metal particle, the graphitic material, or both of them. The method described herein may increase the electrical contact and can also provide the mechanism for chemical contact between metal particles and polymer. By incorporating functionalized graphitic materials, a stronger electrical connection may exist between the metal particle and the metal substrate. The metal particles may be nanoparticles or microparticles. Within the method described herein, the orthogonal chemistries may assist in the attachment of metal particles and polymers with the graphitic material through covalent bonding. Orthogonal chemistries may not interfere with each other. The orthogonal chemistries may happen at ambient conditions. However, orthogonal chemistries may also use UV, IR, or some other curing method.

Figure 8:
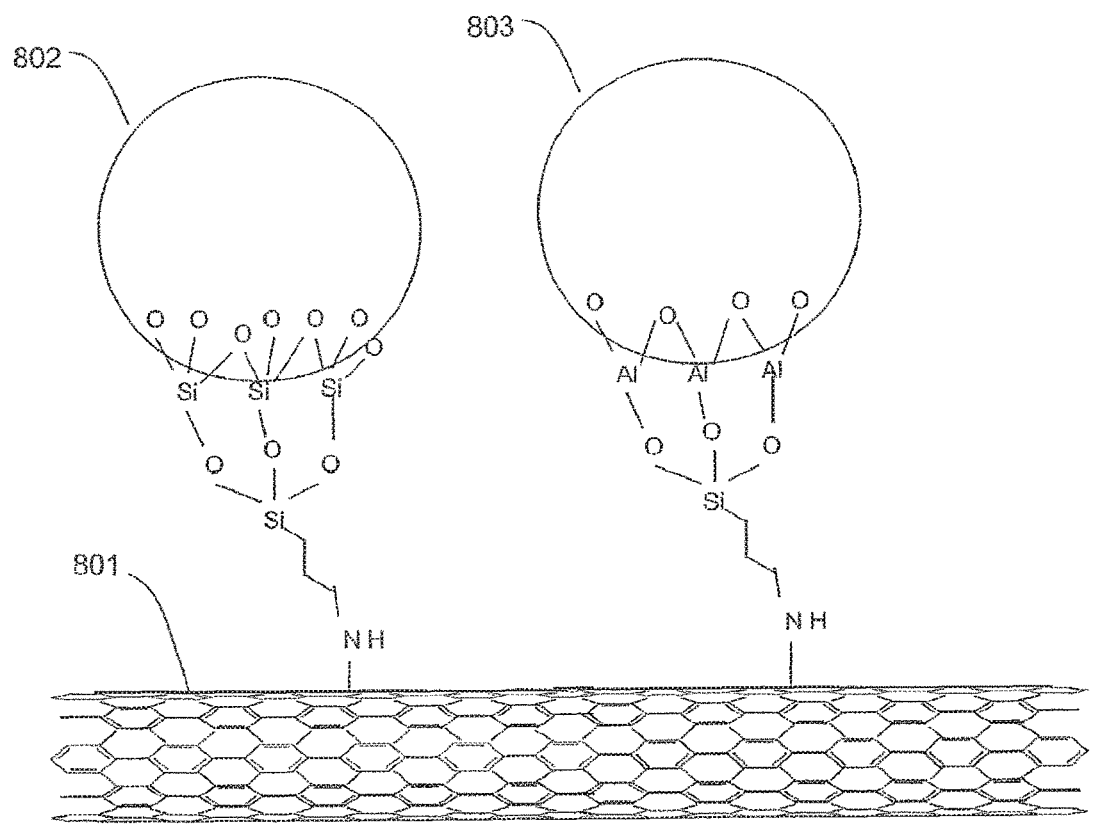
FIG. 8 schematically illustrates what is disclosed herein.

FIG. 8 may provide a means in which to bind ceramic or metallic particles to the functionalized graphitic material. Besides polymeric binding described above, single particles may also be bound. In FIG. 8, the CNT 801 may be shown. Both silica ($SiO_2$) 802 and aluminum oxide ($Al_2O_3$) 803 may be bound to the CNT 801 through the trialkoxysiloxane group. Trimethoxysilane groups may also be able to bind silica or aluminum oxide. Further, a sacrificial metal particle may be bound to the trialkoxysiloxane group. The sacrificial metal particle may comprise at least one metal of zinc, magnesium, nickel, aluminum, and cobalt. Within the methods described herein, the sacrificial metal particle may be in electrical contact with the graphitic material. Within the electrical contact, the spacer may be less than about 1 nm in length, and electron tunneling may occur between the CNT 801 and a metallic particle.

The method described herein may provide a means to avoid passivation of sacrificial particles. Most binding groups (for example, the third group 103 in FIG. 1) may not be bound by sacrificial particles. If the distance between these groups is about 0.4 nm to about 2 nm on the average, then transfer of metal cations may be possible through ionic conductance. With ionic conductance, sacrificial metal cations may be removed from the surface of the particle after oxidative reaction, and the active metal surface may then be exposed. The third groups (shown as 103 in FIG. 1) may be selective for the sacrificial metal cations. This method may allow electronic and ionic conductance along functionalized graphitic material. However, a high degree of functionalization may decrease the electric conductance, especially if single-walled CNTs are used. The effect may be less for double-walled CNTs and multi-walled CNTs. The density of ligands may be smaller if polymeric ionic conductors are attached with graphitic material. Nonlimiting examples of polymeric ionic conductors may be diamino polyethylene oxide, polyallylamine, and polypyrrolidine.

Figure 9:
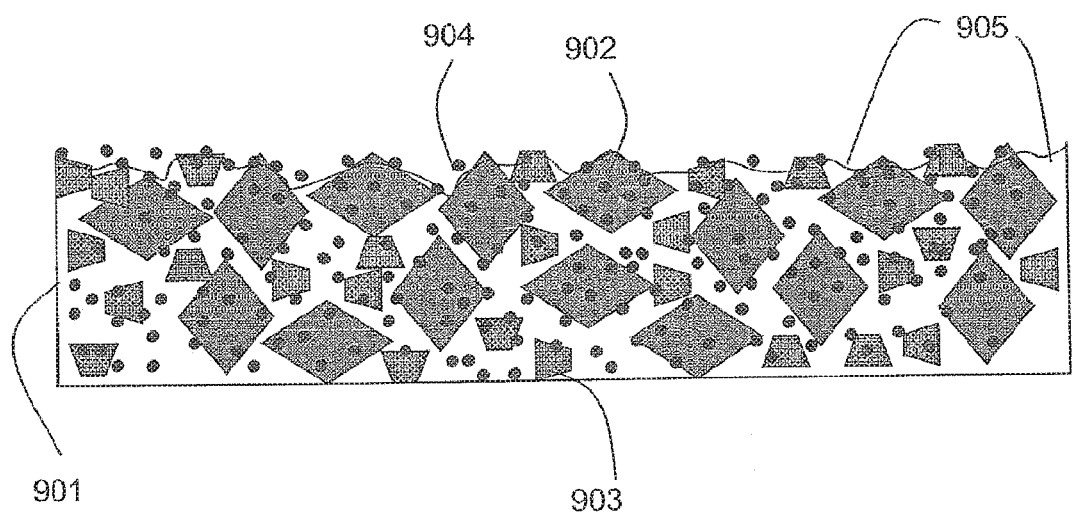
FIG. 9 schematically illustrates what is disclosed herein.

FIG. 9 may provide a pictorial view one embodiment of the tunable material 801 as described herein. The tunable material composition may comprise: 1) a thermoset plastic; 2) silicone; and 3) at least one functionalized graphitic material of carbon nanotubes and graphene prepared by the method comprising the steps of: 1) providing a graphitic material; 2) providing a first molecule comprising a first amino group, a spacer, and a trialkoxysiloxane group; 3) providing a second molecule comprising a second amino group, a spacer, and a third amino group; and 4) bonding the first amino group and the second amino to the graphitic material. Alternatively, the method of providing at least one functionalized graphitic material may be prepared by other methods described above in FIG. 2. The first molecule comprising a first amino group, a spacer, and a trialkoxysiloxane group may be bound to the graphitic material before the second molecule comprising a second amino group, a spacer, and a third amino group, or the second molecule may be bound to the graphitic material before the first molecule. Additionally, the first molecule comprising a first amino group, a spacer, and a trialkoxysiloxane group may bound simultaneously with the second molecule comprising a second amino group, a spacer, and a third amino group, as described in the method above. Also, combinations of the above methods may also be used. As also described in FIG. 7, other materials may be included within the composition in FIG. 7. The tunable material 901 may also contain at least one particle of macroparticles 902, microparticles 903, and nanoparticles 904; a thermoset plastic; silicone; at least one graphitic material of carbon nanotubes and graphene; and a means for providing at least one graphitic material of carbon nanotubes and graphene by high pressure hydrodynamic injection.

Within the tunable material 901 in FIG. 9, macroparticles 902, microparticles 903, and nanoparticles 904 may be dispersed through the thermoset plastic 905. The thermoset plastic may include at least one plastic of an epoxy, a polyurethane, a polyacrylate, and a phenolformaldehyde. In FIG. 9, at least one particle of macroparticles 902, microparticles 903, and nanoparticles 904 may be added. Macroparticles 902 may dimension between about 100 μm to about 2 mm. Microparticles 903 may be about 200 nm to about 100 μm. Nanoparticles 904 may be about 1 nm to about 200 nm. The macroparticles 902 may comprise at least one macroparticle of sand, glass, basalt, alumina, silica, titanium dioxide, ceramic, graphite fibers, and other metal particles. The microparticles 903 may comprise at least one microparticle of titanium dioxide, silica, ceramic, graphite, iron phosphate, alumina, nickel, cobalt, zinc, aluminum, magnesium, and other metal particles. The nanoparticles 904 may comprise at least one nanoparticle of titanium dioxide, copper oxide, iron phosphate, silver, silica, alumina, and other metal particles. The macroparticles 902, microparticles 903, and nanoparticles 904 may also provide desired characteristics to the tunable material 901, depending on the application. For example, titanium dioxide, silica, and alumina particles may increase rigidity and surface hardness. Also, titanium dioxide may be used to provide the tunable material 901 with a self-cleaning property and the Lotus effect. Further, a sacrificial metal particle may added to the tunable material where the sacrificial metal particle may comprise at least one metal of zinc, magnesium, nickel, aluminum, and cobalt.

Additionally, glass and basalt fibers can be metal silicates containing mainly alkali metals, earth alkali metals, and aluminum. Glass may contain borate, while basalt fiber may contain several other metal cations. APTMS can bind with silicic acid or metal cations. The APTMS may react slowly with ionized form of silicic acid. Thus, treating glass and basalt fiber with an acid, either gaseous or liquid, may improve the reaction time. These acids may include, but are not limited to, dilute hydrochloric, sulfuric, formic, and acetic acids. Short treatment with an acid like hydrofluoric acid or ammonium fluoride is also possible. The carbon fiber within the tunable material 801 may have oxygen containing functionalities, such as carboxylic and hydroxylic groups, and the trimethoxysilane group of APTMS may be able to bind with these functionalities.

The tunable material 901 may also comprise at least one functionalized graphitic material, including carbon nanotubes and graphene prepared from the methods described herein. The functionalized graphitic material may be used to reinforce thermoset resins, including but not limited to epoxy and polyurethane resins. Functionalized graphitic material, for instance functionalized carbon nanotubes, may provide a high tensile strength and rigidity. The improved tensile strength and rigidity may offset the moldable thermoset plastic 905.

Within the tunable material 901, silicone may also be added. The silicone within the tunable material 901 can be used to adjust elasticity within the material. The silicone within the tunable material 901 may contain a siloxane structure, and it may be soft and deformable. The amount of silicone within the tunable material 901 may be adjusted to provide a durable material.

Each component of the present tunable material 901 may provide functionality. A thermoset resin 905 may constitute greater than about 90% of the total mass of the composite. The range for macroparticles 902, microparticles 903, and nanoparticles 904 may be about 5% to about 80%, depending of the desired hardness. The range for macroparticles 902, microparticles 903, and nanoparticles 904 may also be about 10% to about 35%. Siloxane can be as low as about 0.05% where it may act within the interface of the matrix and particles. When siloxane may act as a component of the matrix of the tunable material 901, it may range from about 0.1% to about 50%, depending on the desired elasticity. Functionalized graphene may be about 0.1% to about 5%. Mechanical properties may improve between about 0.3% and about 0.8%, but electrical conductivity may improve at about 2%. Within the tunable material 901, the composition can vary, depending upon the application and characteristics desired.

Within the tunable material composition described herein, titanium dioxide nanoparticles may electronically activate oxygen molecules in light. Activated oxygen may then be able to oxidize organic impurities on the surface. Thus, the fabrication of self-cleaning surfaces can be possible. However, the surface itself may be oxidized. Two methods can be used to prevent the oxidation of the surface. The first method may be to increase the inorganic particle concentration. The second method may be to add fluorinated compounds, such as polyfluoro carboxylic acids, alcohols, or aromatic compounds that are chemically bound, for example, with functionalized carbon nanotubes or silicone.

Particles may increase hardness and abrasion resistance of a surface. Pigments may also be used to give a certain color. For example, titanium dioxide macroparticles and microparticles can provide a white color, despite of the presence of black functionalized carbon nanotubes. Titanium dioxide nanoparticles may also provide a self-cleaning surface.

Within the tunable material 901, there may be covalent bonding within all of the components, including the thermoset plastic 905, siloxane, functionalized carbon nanotubes, macroparticles 902, microparticles 903, and nanoparticles 904, including silica, alumina titanium oxide, copper oxide, iron phosphate, carbon, glass, and basalt fiber if these components are present. In a tunable material 901, the components may be in close vicinity of each other, and each component may provide a chemical coupling at molecular level with the neighboring component. Trimethoxysilane groups may also be able to bind glass fiber or basalt fiber when the liquid mixture of the epoxy and hardener may be brought into contact with those fibers, functionalizing the carbon nanotubes. This can be achieved by mixing APTMS with a diamine or polyamine hardener before the functionalization.

The surface may contain macroparticles 902 that are embedded and chemically bound with a polymer matrix. Macroparticles 902 can be sand, glass powder, basalt, silica, alumina, titanium dioxide, graphite fibers, or almost any ceramic material. Microparticles 903 may fill the voids between macroparticles 902, and help to make the surface smoother. The surface may have both microparticle and nano scale roughness. Micro scale roughness can aid in aerodynamics, and nano scale roughness may give a hydrophobic surface or Lotus effect. Nano scale roughness can be achieved by nanoparticles 904.

Within the method described herein, the preparation of graphene or CNT may also incorporate at least one particle of nanoparticles and microparticles into the carbon dispersion, and at least one particle of nanoparticles and microparticles within the second carbon dispersion. Both nanoparticles and microparticles may help with the exfoliation of the graphene or CNT, and can prevent reassembly of graphene back to graphite. The addition of a least one of the nanoparticles and microparticles may include silica, alumina, carbon nanotubes, and amorphous carbon.

Figure 10:
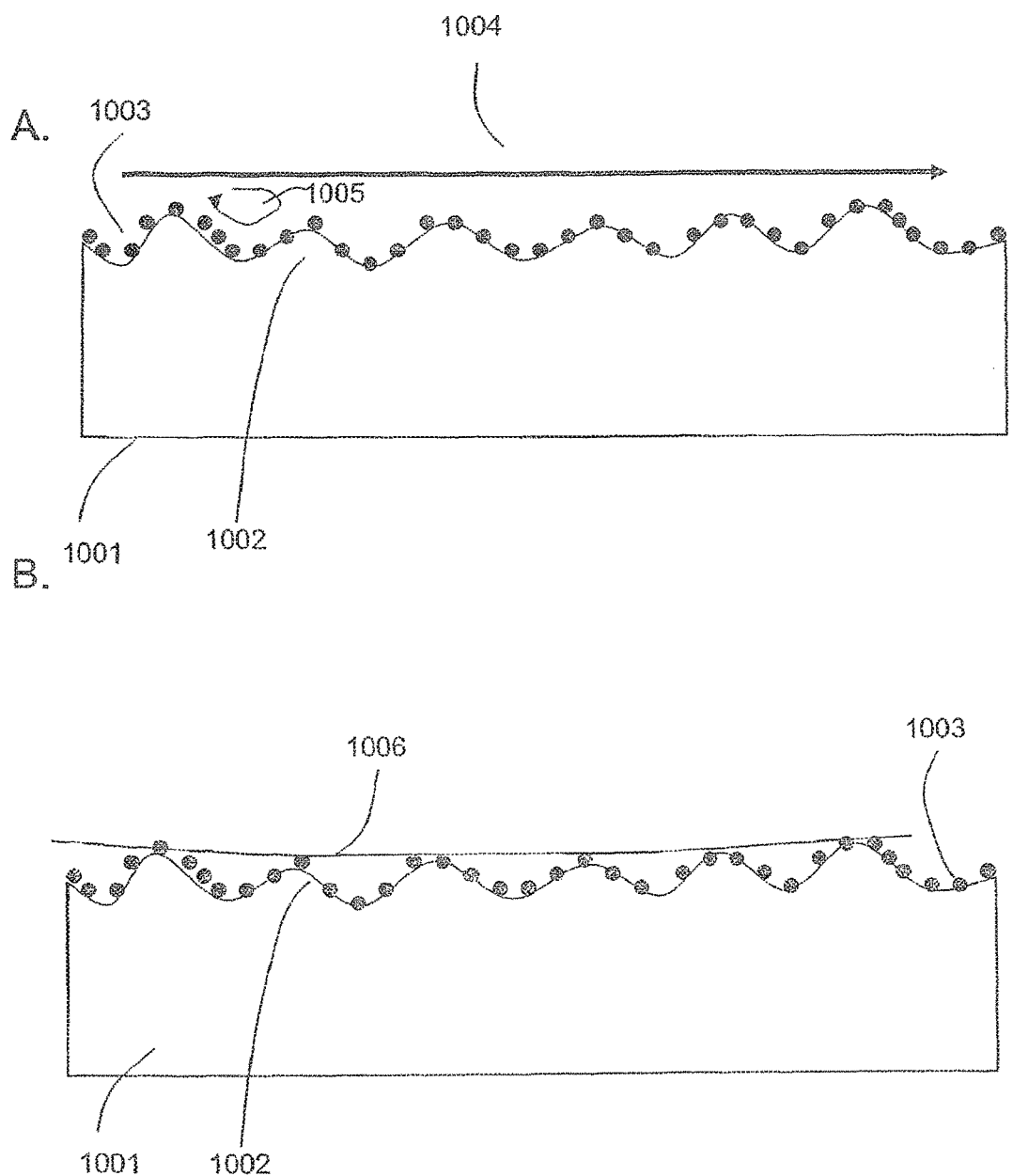
FIG. 10 schematically illustrates what is disclosed herein.

FIG. 10 provides a schematic of a surface structure of an abrasion and corrosion resistant coating 1001. The schematic in FIG. 10 may show both micro scale and nano scale surface roughness. This kind of structure may be useful in certain applications such as windmill blades. Microstructure can reduce friction against water 1004 and airflow. Air may then circulate in microsized pockets 1005, and can act like a ball bearing between solid surfaces. Nanoparticles 1003 within the coating surface 1002 may create a nano corrugation that reduces the interaction between water 1006 and the surface beneath the coating. The surface tension of water 1006 can prevent the water from following nano scale variations. Due to weak interaction at nano scale, water may not be able to follow even micro scale corrugation, so that the adhesion of water 1006 may be further reduced and the water 1006 may not be able to penetrate into the corrosion resistant coating 1001. Thus, water 1006 can be totally removed from the coating surface 1002 as well as the coating 1001 itself on the substrate. The removal of water 1006 may be needed in both humid and cold environments where ice formation may hamper the coating 1001.

The materials of the coating 1001 may include conventional epoxies and polyurethanes. In addition, materials of the coating 1001 may be corrosion resistant as well as both chemically and physically durable. In typical coatings, corrosive liquids such as water, acids, and alkalis may seep through nanocracks can then corrode the underlying surface, potentially causing the coating to detach. This process can be reduced or prevented by the use of the present coating described herein. Thermal expansion and contraction cycles within the coating 1001 described herein may not cause nanocracks because carbon nanotubes within the coating 1001 can prevent this cracking. Moreover, siloxane may help the epoxy or polyurethane to be more plastic and resist any cracking. If the coating 1001 is used to protect a surface against water, including salt water, additional protective layers may be needed. Carbon nanotubes and graphene may make the coating 1001 electrically conducting, although the concentration of carbon nanotubes and graphene CNTs and graphene may be kept so low that the resistance can be high.

Besides the tunable coating described herein, a corrosion resistant coatings system may be provided wherein the tunable coating may be incorporated into the system. One embodiment of the method of making a corrosion resistant coating system may comprise the steps of: 1) providing a substrate; 2) applying to the substrate a first layer of a tunable material composition comprising a thermoset plastic; and at least one functionalized graphitic material of carbon nanotubes and graphene prepared by the method comprising the steps of: providing a graphitic material; providing a first molecule comprising a first group, a spacer, and a second group; providing a second molecule comprising a third group, a spacer, and a fourth group, wherein said third group is a different group from said first group; and bonding the second group and the fourth group to the graphitic material; 2) applying a second layer comprising an electrically insulating material to the first layer; and 3) applying to the second layer a third layer of a tunable material composition comprising a thermoset plastic; and at least one functionalized graphitic material of carbon nanotubes and graphene prepared by the method comprising the steps of: providing a graphitic material; providing a first molecule comprising a first group, a spacer, and a second group; providing a second molecule comprising a third group, a spacer, and a fourth group, wherein said third group is a different group from said first group; and bonding the second group and the fourth group to the graphitic material. Within the process, the first group may comprise at least one group of hydroxyl, thiol, amino, epoxy, carboxyl, and silyl, and the second group may comprise at least one group of amino, epoxy, hydroxyl, carboxyl, silyl, and thiol. Also within the process described herein, the third group may comprise at least one group of thiol, carboxyl, trialkoxysilyl, phosphoryl ester, crown ether, cryptand, dioxime, and N-heterocycle, and the fourth group may comprise at least one group of amino, epoxy, hydroxyl, carboxyl, silyl, and thiol.

Another embodiment of the method of making such a corrosion resistant coating system may comprise the steps of: 1) providing a substrate; 2) applying to the substrate a first layer of a tunable material composition comprising a thermoset plastic; silicone; and at least one functionalized graphitic material of carbon nanotubes and graphene prepared by the method comprising the steps of providing a graphitic material; providing a first molecule comprising a first amino group, a spacer, and a trialkoxysiloxane group; providing a second molecule comprising a second amino group, a spacer, and a third amino group; and bonding the first amino group and the second amino to the graphitic material; 3) applying a second layer comprising an electrically insulating material to the first layer; and 4) applying to the second layer a third layer of a tunable material composition comprising a thermoset plastic; silicone; and at least one functionalized graphitic material of carbon nanotubes and graphene prepared by the method comprising the steps of providing a graphitic material; providing a first molecule comprising a first amino group, a spacer, and a trialkoxysiloxane group; providing a second molecule comprising a second amino group, a spacer, and a third amino group; and bonding the first amino group and the second amino to the graphitic material. Alternatively, the method of making such a corrosion resistant coating system may comprise the steps of: 1) providing a substrate; 2) applying to the substrate a first layer of a tunable material composition comprising a thermoset plastic; silicone; and at least one functionalized graphitic material of carbon nanotubes and graphene prepared by the method comprising the steps of providing a graphitic material; providing a first molecule comprising a second amino group, a spacer, and a third amino group; providing a second molecule comprising a first amino group, a spacer, and a trialkoxysiloxane group; and bonding the first amino group and the second amino to the graphitic material; 3) applying a second layer comprising an electrically insulating material to the first layer; and 4) applying to the second layer a third layer of a tunable material composition comprising a thermoset plastic; silicone; and at least one functionalized graphitic material of carbon nanotubes and graphene prepared by the method comprising the steps of providing a graphitic material; providing a first molecule comprising a second amino group, a spacer, and a third amino group; providing a second molecule comprising a first amino group, a spacer, and a trialkoxysiloxane group; and bonding the first amino group and the second amino to the graphitic material. Within the functionalized graphitic material of carbon nanotubes and graphene prepared by the methods described herein, the molecule comprising an amino group, a spacer, and a trialkoxysiloxane group may be added simultaneously with the molecule comprising an amino group, a spacer, and an additional amino group. Also, combinations of the above methods may also be used.

The primer (undercoat first layer) cannot sacrifice the physical integrity of the coating.

The undercoat first layer may comprise a first tunable material composition. The primer may also contain at least one sacrificial metal particle of magnesium, zinc, nickel, and cobalt. This undercoat first layer may provide galvanic protection against corrosion. The middle layer, or second layer, may be electrically insulating and can contain reinforcements including but not limited to at least one reinforcing material of silicon carbide whiskers, aluminum oxide fibers or tubes, hydrogenated graphene, hydrogenated nanotubes, and carbon nanotubes. The top coat, or third layer, may contain at least one graphitic material of carbon nanotubes and graphene that may be functionalized within the second tunable material composition. The top coat, or third layer, may also contain an optionally biocidic compound as well as particles that may make the coating self-healing and corrosion resistant. The top coat, or third layer, may or may not be identical to the undercoat first layer comprising the first tunable material composition.

The present coating described in FIGS. 9 and 10 and herein may be used in, but may not be limited to, applications with vehicles, boats, ships, oil and gas pipes, and windmill blades. The tunable material composition is used in anticorrosive coatings in electromagnetic interference shields, magnetic shields, conductors, super capacitors, pre-impregnated composites.

The following examples illustrate the present methods in a way that it can be practiced, but as such these examples should not be interpreted as limitations upon the overall scope of the methods described herein.

EXAMPLE 1

Multiwalled CNTs (10 g, Baytubes, Bayer, Germany) and 10 g of aminopropyl trimethoxysilane were sonicated in 1000 g Jeffamine ED-900 hardener (Huntsman, USA) using 1 g aluminum tripropoxide as catalyst. Power was 800 W and the time was about 10 min. This hardener, denoted as HNT-hardener, was ready to be used with bisphenol A epoxy that contained 80 ml of dimethyl dimethoxysilane and 20 g of diphenyl dimethoxysilane.

EXAMPLE 2

Multiwalled CNTs (10 g, Baytubes, Bayer, Germany), 5 g of silica and 5 g of alumina nanoparticles, and 10 g of aminopropyl trimethoxysilane were ground about 30 minutes in mortar in 100 ml Jeffamine ED-900 hardener (Huntsman, USA). This hardener was diluted to 1000 g with neat Jeffamine HK-511, and denoted as HNT-NP-hardener, was ready to be used with 1450 g of bisphenol A epoxy that contained 80 ml of dimethyl dimethoxysilane and 20 g of diphenyl dimethoxysilane.

EXAMPLE 3

The material of Example 2 was diluted with 200 ml of isopropanol, filtered, and washed with 100 ml of isopropanol. The solid was dried under vacuum. Functionalized CNTs were dispersed into 1000 ml of 3,3'-dimethyl-4,4'-diaminodicyclohexylmethane.

EXAMPLE 4

Into 1 kg of bisphenol A diglycidyl ether, 10 g of graphite powder (200 mesh, Alfa Aesar) was added using mechanical mixing. The mixture was degassed in a bath sonicator under nitrogen. The crude graphite dispersion was processed with LV1 Microfluidizer Processor IDEX Material Processing Technologies Group) three times using 1500000 mmHg (2500 bar) pressure.

EXAMPLE 5

The product from Example 3 was mixed with 100 g of zinc powder in a closed metal can using roller mixer. The coated zinc powder was further mixed with high speed mechanical mixer with Epon 828. Melamine curing agent was added, and six test plates were coated with 20 micrometer layer of this coating material. Polyurethane topcoat was applied onto these plates. Six reference plates were similarly coated with a composition that contained the same components, but CNTs were used instead of the amino-trimethoxysilane-CNT. The plates were tested in salt-fog chamber 1000 hours. Rust was measured colorimetrically. The plates that were coated with this method had about 24±11% less rust formation.

The implementations have been described, hereinabove. It will be apparent to those skilled in the art that the above methods and apparatuses may incorporate changes and modifications without departing from the general scope of these methods. It is intended to include all such modifications and alterations in so far as they come within the scope of the appended claims or the equivalents thereof.

What is claimed is:

1. A corrosion resistant coating system comprising:
    a substrate;
    a thermoset plastic; and
    an anticorrosive coating prepared by the method comprising the steps of:
        providing a sacrificial metal particle selected from the group consisting of magnesium, aluminum, zinc, nickel, cobalt, and combinations thereof;
        chemically binding a graphitic material to a first molecule comprising a first group, a first spacer, and a second group, wherein the first group comprises at least one of hydroxyl, thiol, amino, epoxy, carboxyl, and silyl, wherein the second group comprises at least one of amino, epoxy, hydroxyl, carboxyl, silyl, and thiol;
        chemically binding the graphitic material to a second molecule comprising a third group, a second spacer, and a fourth group, wherein the third group is a different group from the first group, wherein the third group comprises at least one of thiol, carboxyl, trialkoxysilyl, phosphoryl ester, crown ether, cryptand, dioxime, and N-heterocycle, wherein the fourth group comprises at least one of amino, epoxy, hydroxyl, carboxyl, silyl, and thiol;
        binding the sacrificial metal particle to either the first or the third group;
        binding either the first or the third group to the substrate, wherein the group bound to the substrate is different from the group bound to the sacrificial metal particle;
        chemically binding the second group and the fourth group to the graphitic material;
        growing thermoset resin side chains on the graphitic material; and
        growing elastomer side chains on the graphitic material.

2. The system of claim 1, wherein the thermoset plastic is at least one plastic of an epoxy, a polyacrylate, a polyurethane, and a phenolformaldehyde.

3. The system of claim 1, wherein the graphitic material is at least one material of carbon nanotubes and graphene.

4. The system of claim 1, wherein the graphitic material is functionalized with at least one hardener of diaminobenzene, diamino polyethyleneoxide, diamino polypropyleneoxide, diamine cyclohexane derivatives, and aminated tall oil.

5. The system of claim 4, further comprising at least one particle of macroparticles, microparticles, and nanoparticles.

6. The system of claim 5, wherein the least one particle is at least one of macroparticle, the macroparticles comprise at least one macroparticle of sand, glass, basalt, alumina, silica, titanium dioxide, ceramic, and graphite fibers; microparticle, said microparticles comprise at least one microparticle of titanium dioxide, silica, ceramic, graphite, iron phosphate, alumina, nickel, cobalt, zinc, aluminum, and magnesium; and nanoparticles, the nanoparticles comprise at least one nanoparticle of titanium dioxide, copper oxide, iron phosphate, silver, silica, and alumina.

7. The system of claim 1, wherein the system composition is used in anticorrosion coatings for electromagnetic interference shields, magnetic shields, conductors, super capacitors, and pre-impregnated composites.

8. The system of claim 1, wherein the elastomer side chain is siloxane.

9. A corrosion resistant coating system comprising:
    a substrate;
    a thermoset plastic;
    silicone; and
    an anticorrosive coating prepared by the method comprising the steps of:
        providing a sacrificial metal particle selected from the group consisting of magnesium, aluminum, zinc, nickel, cobalt, and combinations thereof;
        chemically binding a graphitic material to a first molecule comprising a first group, a first spacer, and a second group, wherein the first group comprises at least one of hydroxyl, thiol, amino, epoxy, carboxyl, and silyl, wherein the second group comprises at least one of amino, epoxy, hydroxyl, carboxyl, silyl, and thiol;

chemically binding the graphitic material to a second molecule comprising a third group, a second spacer, and a fourth group, wherein the third group is a different group from the first group, wherein the third group comprises at least one of thiol, carboxyl, trialkoxysilyl, phosphoryl ester, crown ether, cryptand, dioxime, and N-heterocycle, wherein the fourth group comprises at least one of amino, epoxy, hydroxyl, carboxyl, silyl, and thiol;

binding the sacrificial metal particle to either the first or the third group;

binding either the first or the third group to the substrate, wherein the group bound to the substrate is different from the group bound to the sacrificial metal particle;

chemically binding the second group and the fourth group to the graphitic material;

growing thermoset resin side chains on the graphitic material; and growing elastomer side chains on the graphitic material.

10. The system of claim 9, wherein the thermoset plastic is at least one plastic of an epoxy, polyacrylate, polyurethane, and phenolformaldehyde, wherein the graphitic material is at least one material of carbon nanotubes and graphene, wherein the graphitic material is functionalized with at least one hardener of diaminobenzene, diamino polyethyleneoxide, diamino polypropyleneoxide, diamine cyclohexane derivatives, and aminated tall oil.

11. The system of claim 9, further comprising at least one particle of macroparticles, microparticles, and nanoparticles.

12. The system of claim 11, wherein the least one particle is at least one of macroparticle, the macroparticles comprise at least one macroparticle of sand, glass, basalt, alumina, silica, titanium dioxide, ceramic, and graphite fibers; microparticle, the microparticles comprise at least one microparticle of titanium dioxide, silica, ceramic, graphite, iron phosphate, alumina, nickel, cobalt, zinc, aluminum, and magnesium; and nanoparticles, the nanoparticles comprise at least one nanoparticle of titanium dioxide, copper oxide, iron phosphate, silver, silica, and alumina.

13. The system of claim 12, wherein the system is used in electromagnetic interference shields, magnetic shields, conductors, super capacitors, and pre-impregnated composites.

14. The system of claim 9, wherein the elastomer side chain is siloxane.

* * * * *